United States Patent [19]

Yano et al.

[11] Patent Number: 5,753,466
[45] Date of Patent: May 19, 1998

[54] METHOD FOR RECOVERING DNA FROM SOIL

[75] Inventors: Tetsuya Yano, Isehara; Masahiro Kawaguchi, Atsugi, both of Japan

[73] Assignee: Canon Kabushiki Kaisha, Tokyo, Japan

[21] Appl. No.: 755,350

[22] Filed: Nov. 25, 1996

Related U.S. Application Data

[63] Continuation of Ser. No. 352,886, Dec. 9, 1994, abandoned.

[30] Foreign Application Priority Data

Dec. 13, 1993 [JP] Japan ................ 5-312018

[51] Int. Cl.⁶ .................. C12P 19/34; C12N 1/06; C07H 21/02; C07H 1/08
[52] U.S. Cl. .................. 435/91.1; 435/259; 435/6; 435/9; 435/34; 536/25.4; 536/22.1; 536/127; 536/23.1
[58] Field of Search .................. 435/91.1, 259, 435/6, 9, 34; 536/25.4, 22.1, 127, 23.1

[56] References Cited

U.S. PATENT DOCUMENTS 3,954,726  5/1976  Fiecchi .................. 536/27.31

OTHER PUBLICATIONS

Steffan, et al., "Recovery of DNA from Soils and Sediments," Appl. and Environmental Microbiology, vol. 54, No. 12, pp. 2908–2915 (1988).

Torsvik et al, Appl. Environ. Microbiol. 56(3):782–787 (1990).

Tsai et al, Appl. Environ. Microbiol. 57(4):1070–1074 (1991).

Pillai et al, Appl. Environ. Microbiol. 57(8):2283–2286 (1991).

Bruce et al, Appl. Environ. Microbiol. 58(10):3413–3416 (1992).

*Primary Examiner*—Leon B. Lankford, Jr.
*Assistant Examiner*—Francisco C. Prats
*Attorney, Agent, or Firm*—Fitzpatrick, Cella, Harper & Scinto

[57] ABSTRACT

A method of recovery of DNA of a microorganism in soil is provided which comprises addition of nucleic acid to a liquid suspension containing the soil and the microorganism before lysis of the microorganism and recovery of the desired DNA.

19 Claims, No Drawings

METHOD FOR RECOVERING DNA FROM SOIL

This application is a continuation of application Ser. No. 08/352,886 filed Dec. 9, 1994, now abandoned.

BACKGROUND OF THE INVENTION

1. Field of the Invention

The present invention relates to a method for recovering DNA of a microorganism in soil.

2. Related Background Art

A great variety of microorganisms exist in soil, and for most of them, even isolation can not be accomplished and culture conditions are not known. Identification of such microorganisms in soil, and investigation of the population thereof involve great difficulty, which hinders research of their microbiological ecology. Hitherto, studies on microbiological ecology have been made by improving methods of isolation and culture conditions. Although many ecologically important microorganisms are thought to exist in the soil, it is said that only a small number, probably 0.1% of the microorganism in soils can be isolated and cultivated by known methods. It is highly important to grasp the ecology of microorganisms which are hard to isolate and culture, not only for the progress of science but also for development of applied technology such as waste water treatment and environmental cleanup.

In recent years, environmental pollution caused by hydrocarbons such as aromatic hydrocarbons, paraffins, and naphthenes, or organic chlorine compounds such as trichloroethylene and perchloroethylene has become a serious problem. Strongly desired are technologies for prevention of further expansion of such serious environmental pollution and for cleaning and recovering the environment. Conventional techniques for soil environment remediation includes physicochemical treatments, e.g., aeration, sun bleaching, vacuum vessel treatment, vacuum extraction, etc. However, these physicochemical treatments are not satisfactory due to their operation cost, operability, energy consumption, treatment capacity, their inability to decompose hardly-decomposing substances, and so forth. Therefore, much hope is laid on environment remediation techniques using microorganisms.

There are a number of known microorganisms which can decompose the soil-polluting, hardly decomposable compounds such as aromatic hydrocarbons and organic chlorine compounds. Such microorganisms have been practically applied in polluted soil to decompose polluting substances. Further, field application of a recombinant microorganism of improved decomposition ability has been also studied. To generalize and fix the microbiological technology in the field of soil remediation or of agricultural production as a useful technology, it is highly important to grasp growth and survival of the microorganism in the environment to which it is applied, as well as to develop useful microorganisms.

Conventionally, the growth and survival of a recombinant microorganism in the environment has been studied by estimating the number of viable cells into which a marker gene of antibiotic-resistance, pigment-productivity, etc. was introduced. This technique involves drawbacks such as falling-off of the marker gene, mutation, measurement limit of viable cell count and so forth. It is also pointed out that field application of an antibiotic-resistant microorganism involves epidemiological problems. Furthermore, few methods have been established to grasp the ecology of hard-to-isolate and hard-to-cultivate microorganisms. With recent development of molecular biology, DNA detection technique has become available for detection of recombinants or hard-to-isolate and hard-to-cultivate microorganisms.

When DNA is used as a detection means, total DNA including the DNA of the intended microorganism should be recovered from the environmental sample. Two methods are known for recovering the microorganism-derived DNA from soil: Cell recovery method and Direct cell-lysis method.

In the cell recovery method, microbial cells are collected from the soil and then DNA is isolated from the collected cells. In the direct cell-lysis method, microbial cells are lysed directly in the soil sample and then DNA is recovered.

The cell recovery method has disadvantages that the recovery rate of the microorganism in soil greatly varies depending on the soil, e.g., about 40% from one soil and about 10% from another soil, and that the amount of the recovered DNA is as small as from 1 µg to 100 µg per 100 g of soil. However, this cell recovery method has advantages in that the origin of the recovered DNA is authentic and that purity of DNA is high.

The direct cell-lysis method has a remarkable advantage in that the amount of the recovered DNA is as high as 1 to 2 mg per 100 g of soil, 10 to 100 times that of cell-extraction method. However, disadvantageously the source of the recovered DNA is not clear. That is, together with the DNA of the intended microorganism, all sorts of non-decomposed DNA are recovered from dead bacteria, mold, protozoa, etc. as well as from plants.

A further important problem common to the both methods is the adsorption of cell-derived DNA to soil particles or soil organic substances during the recovery process. From soil of a low cell concentration, sometimes no DNA is recovered.

Generally, from an nutrient-rich environment such as sediment and leaf mold where a huge number of microorganisms exist, a sufficient amount of DNA is recoverable by either of these methods, and specific microbial cells can be detected when the recovered DNA is suitably purified, and suitably detected. However, the quantitative estimation of the cells is considered to be biased to some extent because the adsorption of the DNA by the soil particles and organic substances is not estimated. The adsorption of the DNA is considered to affect also the detection limit. For instance, from the soil containing a small number of living cells, e.g., $10^6$ cells per 1 g of soil, the amount of recoverable DNA is extremely small (the amount of chromosomal DNA for $10^6$ cells being about 5 ng), and such a small amount of DNA may be adsorbed entirely by the soil particles and organic substances, resulting in no DNA recovery.

In utilizing DNA for detection of a microorganism in soil, the technique of recovering DNA from microbial cells is essential, and the conventional methods involve disadvantages described above.

SUMMARY OF THE INVENTION

The present invention intends to provide a method for recovering the DNA of a microorganism in soil at a high recovery ratio without adsorption of the recovered DNA to the soil particles and soil organic compounds. The method of recovery of DNA of a microorganism in soil of the present invention comprises addition of an anionic substance to a liquid suspension containing soil and the microorganism.

DESCRIPTION OF THE PREFERRED EMBODIMENT

From the above viewpoint, the inventors of the present invention studied the recovery method of microbial DNA from soil, and found that anionic substances can prevent adsorption of microorganism-derived DNA to the soil particle or other substances in the sample dispersion and thereby the present invention has been completed.

The present invention is described below more specifically.

The main feature of the present invention is addition of an anionic substance to a sample suspension (a liquid suspension) containing soil and microbial cells.

The anionic substance useful in the present invention includes inorganic ionic compounds such as hydrochloric acid, sulfuric acid, phosphoric acid, arsenic acid, nitric acid, and selenic acid; and organic ionic compounds such as nucleic acid. Of these ionic compounds, nucleic acid is preferred because of its similar physical and chemical properties to the microbial DNA. Since the organic ions like nucleic acid are larger in size and have more complicated structure than inorganic ions, the adsorption of an organic ion like nucleic acid onto soil particles or organic matters is effected by hydrogen bonding and Van der Waals bonding, and stereochemical properties in addition to the electrostatic bonding. Therefore, nucleic acid such as DNA or RNA having properties analogous to DNA, is preferred in effectively blocking the adsorption sites on soil particles for the microorganism-derived DNA.

DNA as the anionic substance includes ordinarily used DNA such as those derived from calf thymus, salmon testes, herring sperm. *E. coli*, and so forth, but is not limited thereto. The RNA includes various ribosomal RNA, transfer RNA, etc.; more specifically including RNAs derived from baker's yeast, calf liver, tolura yeast, fetal calf thymus, wheat germ, bovine liver, *E. coli*, rabbit liver, brewer's yeast, and so forth, but is not limited thereto.

When an ordinary method is employed for the DNA detection, RNA is preferably used as the anionic substance.

The anionic substance is added preferably in an amount corresponding to the adsorption capacity of the sample soil to the anionic substance which can be preliminarily estimated. This amount depends on the characteristics of the sample soil, and the employed anionic substance. Therefore it is preferable to estimate the optimum amount preliminarily.

If the anionic substance does not affect the detection of the recovered DNA, the anionic substance may be added in excess without preliminary estimation of the absorption capacity.

The anionic substance in the present invention is more preferably added to the liquid suspension containing the microorganism and soil before the microbial cells are disrupted, thereby remarkable effect being achieved. Presumably, the anionic substance added to the sample suspension prior to disruption of the microorganism is adsorbed by the soil particles and other adsorbent, thus prevents the adsorption of the DNA of the microorganism released by cell disruption.

The disruption of the microbial cells may be conducted by any known method including physical methods (e.g., French press, ultrasonifier, vortex mixer, etc.), chemical methods (e.g., surfactant), and enzymatic cell lysis. Such a method is combined with a known recovery method such as direct cell-lysis and cell recovery method to recover the DNA. The direct cell-lysis and the cell recovery method are described in detail in the report by Steffan (Steffan, R. J., J. Goksoyr, A. K. Bej, and R. M. Atlas: "Recovery of DNA from Soils and Sediments", Appl. Environ. Microbiol. 54, 2908–2915 (1988)).

The present invention is described below in more detail without limiting the invention thereby.

EXAMPLE 1

(A) Measurement of anionic substance adsorption capacity of sample soil

Aliquots of 0.5 gram of loam soil sterilized by autoclaving were placed in 2 ml-Eppendorf tubes. To each tube, a certain amount of DNA suspended in 1 ml of TE buffer solution (pH: 8.0) was added (Table 1)(salmon testes, Sigma Co.). After mixing by a vortex mixer, 0.1 ml of 10% SDS (sodium dodecylsulfate) was added thereto and vortexed to mix again. The mixture, after standing at 70° C. for one hour, was centrifuged at 15,000 rpm at 4° C. for 10 minutes in a microcentrifuge. The supernatant was collected and thereto 0.25 ml of 7.5M ammonium acetate solution was added. After standing at room temperature for 5 minutes, the mixture was further centrifuged under the above conditions. The supernatant was collected. Thereto 0.8 ml of isopropanol was added with sufficient agitation, and left standing for 10 minutes at room temperature. The mixture was centrifuged at 15,000 rpm at 15° C. for 10 minutes. The obtained pellet was air-dried. Thereto 50 μl of TE buffer solution (pH: 8.0) was added to dissolve the DNA.

An aliquot of 10 μl of the above DNA solution was subjected to agarose gel electrophoresis. The amount of recovered DNA was estimated by comparison with the agarose gel electrophoresis pattern of HindIII-digested λ-DNA. The results are shown in Table 1.

TABLE 1

| | Recovery of DNA | | | | | |
|---|---|---|---|---|---|---|
| Added DNA (μg) | 0.5 | 1.0 | 2.0 | 4.0 | 8.0 | 16.0 |
| Recovered DNA (μg) | N.D. | N.D. | N.D. | N.D. | N.D. | 1.0 |

N.D. : No DNA detected ( <5 ng )

The above result shows that the adsorption sites of the sample soil can be sufficiently blocked by adding 15 μg of DNA or more as the anionic substance.

(B) Measurement of Quantity of DNA Derived from *E. coli* Strain HB101

In 2-ml Eppendorf tubes, was placed respectively a prescribed amount (Table 2) of HB101 strain of *E. coli* (Takara Shuzo Co.) suspended in 1 ml of 0.1M phosphate buffer solution (pH: 8.0). After mixing by a vortex mixer, 0.1 ml of 10% SDS (sodium dodecylsulfate) was added thereto, and the mixture was agitated by a vortex mixer, and kept standing at 70° C. for one hour. Then the mixture was centrifuged at 15,000 rpm at 4° C. for 10 minutes in a microcentrifuge. The supernatant was collected, to which 0.25 ml of 7.5 M ammonium acetate solution was added. The mixture was left standing at room temperature for 5 minutes, and then centrifuged under the above conditions. To the separated supernatant, 0.8 ml of isopropanol was added. The mixture was mixed sufficiently, and left standing at room temperature for 10 minutes, and centrifuged at 15,000 rpm at 15° C. for 10 minutes in an microcentrifuge. The pellet was recovered and air-dried. Thereto 50 μl of TE buffer solution (pH: 8.0) was added to dissolve the DNA.

A 10 μl aliquot of the above prepared DNA solution was subjected to agarose electrophoresis, and the amount of recovered DNA was measured. The results are shown in Table 2, from which the amount of DNA in each sample can be estimated.

(C) Recovery and Detection of DNA of *E. coli* Injected to Sample Soil (1):

Of loam soil sterilized by autoclaving, 0.5 gram aliquots were placed in 2 ml-Eppendorf tubes respectively. To each tube, was added a prescribed amount (Table 2) of *E. coli* strain HB101 (product of Takara Shuzo Co.) suspended in 1 ml of 0.1M phosphate buffer solution (pH: 8.0). Further thereto, 50 µl (25 mg RNA) of a solution of RNA (produced by Sigma Co., derived from bakers yeast, 500 mg/ml) was added to each tube as the anionic substance of the present invention and mixed by a vortex mixer. 0.1 ml of 10% SDS (sodium dodecylsulfate) was added thereto, and vortexed. The mixture, after standing at 70° C. for one hour, was centrifuged at 15,000 rpm at 4° C. for 10 minutes in a microcentrifuge. The supernatant was collected and thereto 0.25 ml of 7.5M ammonium acetate solution was added. After standing at room temperature for 5 minutes, the mixture was centrifuged under the above conditions. The supernatant was collected and thereto 0.8 ml of isopropanol was added with sufficient agitation, and was left standing for 10 minutes at room temperature. The mixture was centrifuged at 15,000 rpm at 15° C. for 10 minutes. The obtained pellet was air-dried. Thereto 50 µl of TE buffer solution (pH: 8.0) was added to dissolve the DNA.

A 10 µl aliquot of the above DNA solution was subjected to agarose gel electrophoresis. The amount of the recovered DNA was estimated in the same manner as in the above item (A). The results are shown in Table 2.

The results are almost the same as the results obtained in the above item (B), and it was shown that DNA can be nearly completely recovered from even a small number of *E. coli* cells according to the method of the present invention.

COMPARATIVE EXAMPLE 1

Recovery and Detection of DNA of *E. coli* Injected to Sample Soil (2)

0.5 Gram aliquots of loam soil sterilized by autoclaving were placed in 2 ml-Eppendorf tubes respectively. To each tube, was added a prescribed amount (Table 2) of HB101 strain of *E. coli* (product of Takara Shuzo Co.) suspended in 1 ml of 0.1 M phosphate buffer solution (pH: 8.0). After mixing it by a vortex mixer, 0.1 ml of 10% SDS (sodium dodecylsulfate) was added thereto, and vortexed. The mixture, after kept standing at 70° C. for one hour, was centrifuged at 15,000 rpm at 4° C. for 10 minutes in a microcentrifuge. The supernatant was collected and thereto 0.25 ml of 7.5M ammonium acetate solution was added. After standing at room temperature for 5 minutes, the mixture was centrifuged under the above conditions. The supernatant was collected and thereto 0.8 ml of isopropanol was added with sufficient agitation, and was left standing for 10 minutes at room temperature. The mixture was centrifuged at 15,000 rpm at 15° C. for 10 minutes. The obtained pellet was air-dried. Thereto 50 µl of TE buffer solution (pH: 8.0) was added to dissolve the DNA.

An 10 µl aliquot of the above DNA solution was subjected to agarose gel electrophoresis. The amount of the recovered DNA was estimated in the same manner as in the above item (A) of Example 1. The results are shown in Table 2.

*E. coli*-derived DNA could be recovered from the sample soils only when the sample contained a large amount of *E. coli* as much as $10^9$ /ml.

EXAMPLE 2 AND COMPARATIVE EXAMPLE 1

PCR Detection of *E. coli* DNA Added to Sample Soil

It was used DNA solutions prepared in Example 1 (B), Example 1 (C), and Comparative Example 1 and also DNA solutions prepared in the same manner as in Example 1 (B), Example 1 (C), and Comparative Example 1 except that the bacterial cell concentrations were reduced to $10^3$, $10^4$, and $10^5$ cells/ml. The DNA derived from *E. coli* was detected in these samples by PCR method employing a gene encoding 16S ribosomal RNA of *E. coli*. The employed primers were the two shown below:

Primer #1:
5'-AAGGGAGTAAAGTTAATACCTTTG-3'SEQ ID No: 1

Primer #2:
5'-GGCACATTCTCATCTCTGAAA-3'SEQ ID No: 2

With these two primers, an amplification product of about 0.6 Kb can be obtained.

PCR was conducted with the total volume of 50 µl in a 0.5 ml-Eppendorf tube. The reaction mixture was overlaid with mineral oil. The thermal cycler employed was Model PJ-1000 manufactured by Perkin Elmer Cetus Co. The Taq DNA polymerase was AmpliTaq DNA polymerase supplied by Takara Shuzo Co. The buffer solution was sold with the enzyme in a set, and used in the concentration according to the supplier's manual, each dNTP was used at a concentration of 200 µM, and the above two primers were used at a concentration of 0.1 µM respectively. An 1 µl aliquot of the above-prepared DNA solution was added to the above reaction mixture, and further thereto 1.0 unit of Taq DNA polymerase was added, and the mixture was subjected to PCR for 30 cycles of 90° C. for one minute, 55° C. for one minute, and 72° C. for one minute in one cycle. The sample after the PCR was subjected to agarose gel electrophoresis to confirm the presence of the PCR amplification product. The results are shown in Table 2.

In Example 2, DNA from the samples with or without soil could be detected for the bacterial cell concentration of as low as $10^3$ cells/ml. On the contrary, in Comparative Example 2, the DNA could not be detected for the samples of the bacterial concentrations lower than $10^7$ cells/ml.

From the above results, according to the present invention, bacterial cells can be detected satisfactorily at a cell number of as low as $10^3$ cells/ml by combination of PCR amplification method.

TABLE 2

| | | Concentration of *E. coli* (cells/ml) | | | | | | | |
|---|---|---|---|---|---|---|---|---|---|
| | | 0 | $10^3$ | $10^4$ | $10^5$ | $10^6$ | $10^7$ | $10^8$ | $10^9$ |
| Example 1 (B) | Recovered DNA (µg) | x | — | — | — | 0.005 | 0.05 | 0.4 | 3.5 |
| Example 2 (B) | PCR amplification product | x | o | o | o | o | o | o | o |
| Example 1 (C) | Recovered DNA (µg) | x | — | — | — | 0.005 | 0.05 | 0.35 | 3.6 |
| Example 2 (C) | PCR amplification product | x | o | o | o | o | o | o | o |

TABLE 2-continued

| | | Concentration of E. coli (cells/ml) | | | | | | | |
|---|---|---|---|---|---|---|---|---|---|
| | | 0 | $10^3$ | $10^4$ | $10^5$ | $10^6$ | $10^7$ | $10^8$ | $10^9$ |
| Comparative Example 1 | Recovered DNA (µg) | x | — | — | — | x | x | x | 3.2 |
| Comparative Example 2 | PCR amplification product | x | x | x | x | x | o | o | o |

Example 2 (B): cells only, Example 2 (C) cells + soil
Agarose electrophoresis method - x: No DNA detected (<5 ng) PCR method - o: Amplification product found; x: No amplification product found

EXAMPLE 3
Recovery and Detection of DNA Derived from *E. coli* Injected to Soil Sample (3)

0.5 Gram aliquots of loam soil sterilized by autoclaving were placed in 2 ml-Eppendorf tubes respectively. To each tube, was added a prescribed amount (Table 3) of HB101 strain of *E. coli* (product of Takara Shuzo Co.) suspended in 1 ml of 0.1 M phosphate buffer solution (pH: 8.0). For a control, a sample containing no *E. coli* was also prepared. Further thereto, 50 µl (DNA: 15 µg) of a solution of DNA (Salmon testes DNA, product of Sigma Co., 300 µg/ml) was added and mixed by a vortex mixer. Thereto 0.1 ml of 10% SDS (sodium dodecylsulfate) was added, and vortexed. The mixture, after kept standing at 70° C. for one hour, was centrifuged at 15,000 rpm at 4° C. for 10 minutes in a microcentrifuge. The supernatant was collected, and thereto 0.25 ml of 7.5M ammonium acetate solution was added. After standing at room temperature for 5 minutes, the mixture was further centrifuged under the above conditions. The supernatant was collected and thereto 0.8 ml of isopropanol was added with sufficient agitation, and was left standing for 10 minutes at room temperature. The mixture was centrifuged at 15,000 rpm at 15° C. for 10 minutes. The obtained pellet was air-dried. Thereto 50 µl of TE buffer solution (pH: 8.0) was added to dissolve the DNA. (A) A 10 µl aliquot of the above DNA solution was subjected to agarose gel electrophoresis. The amount of the recovered DNA was estimated in the same manner as in Example 1 (A). The results are shown in Table 3.

In this Example, DNA was added as the anionic substance and the excess DNA was also recovered, which made the recovery of DNA larger. (B) The presence of DNA derived from *E. coli* was confirmed by PCR method employing a gene encoding the 16S ribosomal RNA of *E. coli*. The employed primers were the two shown below:

Primer #1:
 5'-AAGGGAGTAAAGTTAATACCTTTG-3' SEQ ID No: 1

Primer #2:
 5'-GGCACATTCTCATCTCTGAAA-3' SEQ ID No: 2

With these two primers, an amplification product of about 0.6 Kb can be obtained.

PCR was conducted with the total volume of 50 µl in a 0.5 ml-Eppendorf tube. The reaction mixture was overlaid with mineral oil. The thermal cycler employed was Model PJ-1000 manufactured by Perkin Elmer Cetus Co. The Taq DNA polymerase was AmpliTaq DNA polymerase supplied by Takara Shuzo Co. The buffer solution was sold with the enzyme in a set, and used in the concentration according to the supplier's manual. Each dNTP was used at a concentration of 200 µM, and the above two primers were used at a concentration of 0.1 µM respectively. An 1 µl aliquot of the above-prepared DNA solution was added to the above reaction mixture, and further thereto 1.0 unit of Taq DNA polymerase was added, and the mixture was applied to PCR for 30 cycles of 90° C. for one minute, 55° C. for one minute, and 72° C. for one minute in one cycle. The sample after the PCR was subjected to agarose gel electrophoresis to confirm the presence of the PCR amplification product. The results are shown in Table 3.

From the results, it was confirmed that DNA from a small number of *E. coli* can be detected using PCR to detect *E. coli*-specific DNA, even when DNA is used as the anionic substance.

TABLE 3

| | | Concentration of E.coli cells/ml | | | | |
|---|---|---|---|---|---|---|
| | | 0 | $10^6$ | $10^7$ | $10^8$ | $10^9$ |
| Example 3 (A) | Recovered DNA (µg) | 1.0 | 1.0 | 1.1 | 2.4 | >5 |
| Example 3 (B) | PCR amplification product | x | o | o | o | o |

Amplification product -- o : detected, x : not detected

EXAMPLE 4
Recovery of DNA from Actual Soil Sample (1)

Samples (0.5 gram) of various soil were placed in 2 ml-Eppendorf tubes. To each tube, 1 ml of 0.1M phosphate buffer solution (pH: 8.0) was added. Further thereto, 50 µl of solution (500 mg RNA/ml) of RNA (Baker's yeast RNA, Sigma Co.) was added, and the mixture was agitated by a vortex mixer. Thereto 0.1 ml of 10% SDS (sodium dodecylsulfate) was added, and vortexed. The mixture, after kept standing at 70° C. for one hour, was centrifuged at 15,000 rpm at 4° C. for 10 minutes in a microcentrifuge. The supernatant was collected, and thereto 0.25 ml of 7.5M ammonium acetate solution was added. After standing at room temperature for 5 minutes, the mixture was centrifuged under the above conditions. The supernatant was collected and thereto 0.8 ml of isopropanol was added with sufficient agitation, and the mixture was left standing for 10 minutes at room temperature. It was centrifuged at 15,000 rpm at 15° C. for 10 minutes. The obtained pellet was air-dried. Thereto 50 µl of TE buffer solution (pH: 8.0) was added to make a DNA solution.

A 10 µl aliquot of the above DNA solution was subjected to agarose gel electrophoresis. The amount of the recovered DNA was estimated in the same manner as in Example 1 (A). DNA was recovered from the samples as in Table 4.

COMPARATIVE EXAMPLE 3
Recovery of DNA from Actual Soil Sample (2)

0.5 Gram samples of various soil were placed in 2 ml-Eppendorf tubes. To each tube, 1 ml of 0.1 M phosphate buffer solution (pH: 8.0) was added, and the mixture was agitated by a vortex mixer. Thereto 0.1 ml of 10% SDS (sodium dodecylsulfate) was added, and the mixture was agitated by a vortex mixer. The mixture, after kept standing at 70° C. for one hour, was centrifuged at 15,000 rpm at 4° C. for 10 minutes in a microcentrifuge. The supernatant was collected, and thereto 0.25 ml of 7.5M ammonium acetate solution was added. After standing at room temperature for 5 minutes, the mixture was further centrifuged under the above conditions. The supernatant was collected and thereto 0.8 ml of isopropanol was added with sufficient agitation, and the mixture was left standing for 10 minutes at room temperature. It was centrifuged at 15,000 rpm at 15° C. for 10 minutes. The obtained pellet was air-dried. Thereto 50 µl of TE buffer solution (pH: 8.0) was added to make a DNA solution.

A 10 µl aliquot of the above DNA solution was subjected to agarose gel electrophoresis. The amount of the recovered DNA was estimated in the same manner as in Example 1 (A). No DNA was recovered from the samples as shown in Table 4.

TABLE 4

| Recovery of DNA from actual soil sample | | | | | |
|---|---|---|---|---|---|
| Sample No. | | 1 | 2 | 3 | 4 |
| Example 4 | Recovered DNA (µg) | 0.45 | 0.75 | 0.14 | 0.52 |
| Comparative Example 3 | Recovered DNA (µg) | x | x | x | x | x : No DNA detected (<5 ng)

What is claimed is:

1. A method of recovering DNA from a microorganism in a soil comprising the steps of:

(a) preparing a first liquid suspension of the soil containing a microorganism containing the DNA to be recovered;

(b) adding a predetermined amount of a first nucleic acid to the first liquid suspension, the first nucleic acid blocking adsorption sites of the soil;

(c) extracting the DNA from the microorganism in the soil of which adsorption sites are blocked; and (d) recovering the extracted DNA, wherein the predetermined amount of the first nucleic acid is sufficient to block all the adsorption sites to be blocked of the soil in the first liquid suspension, the amount of all adsorption sites of the soil to be blocked being determined by the steps of (i) preparing a second liquid suspension of the soil;

(ii) adding a predetermined amount of a second nucleic acid to the second suspension, the second nucleic acid blocking the adsorption sites of the soil; and (iii) measuring a maximum amount of the second nucleic acid trapped in the adsorption sites of the soil in the second suspension.

2. A method according to claim 1, wherein the nucleic acid is selected from the group consisting of (a) DNA different from the DNA derived from the microorganism and (b) RNA.

3. A method according to claim 2, wherein the DNA is selected from the group consisting of DNA derived from calf

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (Synthesized Polynucleotide)

( x i ) SEQUENCE DESCRIPTION: SEQ ID NO:1:

AAGGGAGTAA      AGTTAATACC      TTTG                              24

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (Synthesized Polynucleotide)

( x i ) SEQUENCE DESCRIPTION: SEQ ID NO:2:

GGCACATTCT      CATCTCTGAA      A                                21 thymus, DNA derived from salmon testis, DNA derived from herring sperm and DNA derived from *E. coli*.

4. A method according to claim 2, wherein the RNA is selected from the group consisting of ribosomal RNA and transfer RNA.

5. A method according to claim 2, wherein the RNA is selected from the group consisting of RNA derived from baker's yeast, RNA derived from calf liver, RNA derived from *E. coli*, RNA derived rabbit liver and RNA derived from brewer's yeast.

6. A method according to claim 1, wherein the microorganism is a bacterium.

7. The method according to claim 1, wherein the first nucleic acid is identical to the second nucleic acid.

8. The method according to claim 1, wherein the first nucleic acid employed is RNA.

9. The method according to claim 1, wherein the second nucleic acid employed is DNA.

10. A method for recovering DNA from a microorganism in a soil, comprising the steps of:
   (a) preparing a soil containing a microorganism having DNA to be recovered;
   (b) measuring an amount of adsorption sites to be blocked in the soil by the steps of:
      (i) preparing a first liquid suspension of the soil;
      (ii) adding a predetermined amount of a first nucleic acid to the first suspension, the first nucleic acid being capable of blocking the adsorption sites of the soil; and
      (iii) measuring a maximum amount of the first nucleic acid trapped in the adsorption sites of the soil in the first suspension;
   (c) preparing a second liquid suspension of the soil;
   (d) adding a second nucleic acid capable of blocking the adsorption sites to the second liquid suspension in sufficient amount so that all the adsorption sites are blocked, the amount of the second nucleic acid added based on the amount of the adsorption sites measured in step (b);
   (e) extracting the DNA from the microorganism in the soil of which all the adsorption sites are blocked; and
   (f) recovering the extracted DNA.

11. A method for recovering DNA from a microorganism in a soil, comprising the steps of:
   (a) preparing a first liquid suspension of the soil, the soil containing a microorganism having DNA to be recovered;
   (b) blocking all of adsorption sites of the soil in the first suspension;
   (c) extracting the DNA from the microorganism in the soil in which all said adsorption sites are blocked; and
   (d) recovering the extracted DNA, wherein the amount of the adsorption sites to be blocked is determined by the steps of
      (i) preparing a second liquid suspension of the soil;
      (ii) adding a predetermined amount of a material capable of blocking the adsorption sites of the soil to the second suspension; and
      (iii) measuring a maximum amount of the material trapped in the adsorption sites of the soil.

12. A method of recovering a DNA of a microorganism in a soil comprising the steps of:
   (a) preparing a liquid suspension of a sample of the soil containing the microorganism;
   (b) adding a foreign DNA or RNA obtained from a source different from the microorganism into the liquid suspension in an amount sufficient to block substantially all free adsorption sites of the soil which can adsorb the nucleic acid;
   (c) releasing the DNA from the microorganism; and
   (d) extracting and recovering the DNA from the liquid suspension.

13. The method according to claim 12, wherein the amount of the foreign DNA or RNA added exceeds a maximum capacity of the soil to trap a nucleic acid, said maximum capacity determined by
   (a) preparing a second liquid suspension of the soil containing the microorganism;
   (b) adding varying amounts of the nucleic acid to the second suspension to determine the maximum amount of the nucleic acid the soil can trap; and
   (c) calculating the maximum capacity of the soil to trap the nucleic acid.

14. The method according to claim 13, wherein the nucleic acid employed is the same as the foreign RNA or DNA.

15. The method according to claim 13, wherein the nucleic acid employed is RNA.

16. The method according to claim 13, wherein the nucleic acid employed is DNA.

17. A method of recovering DNA of a microorganism in a soil comprising the steps of:
   (a) forming a liquid suspension containing the soil and a microorganism containing the DNA to be recovered;
   (b) adding at least about 30 µg per gram of said soil of a nucleic acid to the liquid suspension to block DNA adsorption sites of the soil;
   (c) extracting the DNA from the microorganism in the liquid suspension in which the soil having blocked DNA adsorption sites is present; and
   (d) recovering the extracted DNA from the liquid suspension.

18. A method of recovering DNA of a microorganism in a soil comprising the steps of:
   (a) forming a liquid suspension containing the soil and a microorganism containing the DNA to be recovered;
   (b) adding a sufficient amount of a nucleic acid to block DNA adsorption sites of the soil in order to obtain a detectable amount of DNA extracted from $2 \times 10^3$ cells of microorganism per gram of soil by PCR detection;
   (c) extracting the DNA from the microorganism in the liquid suspension in which the soil having blocked DNA adsorption sites is present; and
   (d) recovering the extracted DNA from the liquid suspension.

19. A method according to claim 18, wherein the nucleic acid is RNA.

* * * * *

UNITED STATES PATENT AND TRADEMARK OFFICE
CERTIFICATE OF CORRECTION

PATENT NO. : 5,753,466
DATED : May 19, 1998
INVENTOR(S) : TETSUYA YANO, ET AL.

It is certified that error appears in the above-identified patent and that said Letters Patent is hereby corrected as shown below:

COLUMN 2

Line 21, "purity of" should read --the purity of the--.

COLUMN 3

Line 3, "ticle" should read --ticles--;
    Line 19, "matters" should read --matter--;
    Line 31, "tolura" should read --torula--;
    Line 50, "thereby remarkable effect" should read --a good result thereby--; and
    Line 54, "prevents" should read --preventing--.

COLUMN 5

Line 45, "kept" should be deleted.

COLUMN 6

Line 11, "It was used" should be deleted;
    Line 15, "except" should read --were used except--; and
    Line 35, "each" should read --Each--.

COLUMN 7

Line 27, "kept" should be deleted;
    Line 38, "(A) A 10" should read --¶ (A) A 10--; and
    Line 45, "(B)" should read --¶ (B)--.

UNITED STATES PATENT AND TRADEMARK OFFICE
CERTIFICATE OF CORRECTION

PATENT NO. : 5,753,466

DATED : May 19, 1998

INVENTOR(S) : TETSUYA YANO, ET AL.

It is certified that error appears in the above-identified patent and that said Letters Patent is hereby corrected as shown below:

<u>COLUMN 8</u>

Line 40, "soil" should read --soils--;
    Line 43, "Baker's" should read --baker's--;
    Line 47, "kept" should be deleted; and
    Line 66, "soil" should read --soils--.

<u>COLUMN 9</u>

Line 4, "kept" should be deleted.

<u>COLUMN 11</u>

Line 9, "rabbit" should read --from rabbit--; and
    Line 49, "of" (first occurrence) should read --of the--.

Signed and Sealed this

Twenty-third Day of February, 1999

Attest:

Q. TODD DICKINSON

*Attesting Officer*      *Acting Commissioner of Patents and Trademarks*